United States Patent [19]
Kamer et al.

[11] Patent Number: 5,817,848
[45] Date of Patent: Oct. 6, 1998

[54] BIDENTATE PHOSPHINE LIGAND

[75] Inventors: Paulus C. J. Kamer, Naarden; Mirko Kranenburg, Amsterdam; Petrus W. N. M. van Leeuwen, Kockengen; Johannes G. de Vries, Maastricht, all of Netherlands

[73] Assignee: DSM N.V., Heerlen, Netherlands

[21] Appl. No.: 746,189

[22] Filed: Nov. 6, 1996

Related U.S. Application Data

[63] Continuation of PCT/NL95/00161 May 4, 1995.

[30] Foreign Application Priority Data

May 6, 1994 [BE] Belgium .................... 9400470

[51] Int. Cl.[6] .................... C07F 9/02; C07F 15/00
[52] U.S. Cl. .................... 556/12; 556/18; 556/21; 556/404; 560/402; 568/12; 568/13; 568/17; 502/158; 502/162; 502/166
[58] Field of Search .................... 60/402; 568/12, 568/13, 17; 556/404, 12, 18, 21; 502/158, 162, 166

[56] References Cited

U.S. PATENT DOCUMENTS

| | | | |
|---|---|---|---|
| 4,851,581 | 7/1989 | Devon et al. | 568/17 |
| 4,904,808 | 2/1990 | Devon et al. | 556/21 |
| 5,171,892 | 12/1992 | Burk | 568/12 |
| 5,329,015 | 7/1994 | Burk | 549/10 |
| 5,386,061 | 1/1995 | Burk | 568/12 |

OTHER PUBLICATIONS

Pramesh N. Kapoor, Nickel(II), Palladium(II) and Platinum(II) Complexes of trans Spanning Ditertiary Phosphine 3,3'–Oxybis–[DI–meta–Tolyophosphino)Methyl]Benzene, Journal of Organometallic Chemistry, 1986, vol. 315, No. 3 pp. 383–386.

Matthias W. Haenel, Bidentate Phosphines of Heteroarenes: 4,6–Bis(diphenylphosphino)–dibenzofuran and 4,6–Bis-(diphenylphosphino)dibenzothiophene[1,2], Chemische Berichte, 1991, vol. 124, No. 8 pp. 1705–1710.

Matthias W. Haenel, Bidentate Phosphines of Heteroarenes: 1,9–Bis(disphenylphosphino)–dibenzothiophene and 4,6–Bis(diphenylphosphino)dibenzothiophene[1], 1993, vol. 34, No. 13 pp. 2107–2110.

Stefan Hillebrand, et al., Bidentate Phosphines of Heteroarenes: 9,9–Dimethyl–4,5–bis(diphenylphosphino)xanthene[1], 1995, vol. 36, pp. 75–78.

Chaloner, Handbook of Coordination Catalysis in Organic Chemistry, pp. 403–450, (Butterworths 1986).

*Primary Examiner*—Porfirio Nazario-Gonzalez
*Attorney, Agent, or Firm*—Pillsbury Madison & Sutro

[57] ABSTRACT

The invention relates to a bidentate phosphine ligand, the phosphorus atoms of the phosphine being connected via a bridge group, the bridge group of the bidentate phosphine ligand consisting of an ortho-anellated annular system, comprising two aryl groups, which aryl groups are connected by two bridges, the first bridge consisting of an —O— or an —S— atom and the second bridge being a group that contains an oxygen, sulphur, nitrogen, silicon or carbon atom or a combination of these atoms, the two phosphorus atoms being connected to the two aryl groups of the bridge group at the ortho-position relative to the —O— or —S— atom of the first bridge.

The invention also relates to the use of this bidentate phosphium ligand in a catalyst system comprising also a transition metal compound which is used in the following type of reactions: hydroformylation hydrogenation, hydrocyanation, polymerization, isomerisation, carboxylation, cross coupling and metathesis.

51 Claims, No Drawings

BIDENTATE PHOSPHINE LIGAND

RELATED APPLICATIONS

This is a continuation of International Application No. PCT/NL95/00161 filed May 4, 1995, which designated the U.S.

FIELD OF THE INVENTION

The invention relates to a bidentate phosphine ligand, the phosphorus atoms of the phosphine being connected via a bridge group.

BACKGROUND OF THE INVENTION

A bidentate phosphine ligand is a molecule having the following general structural formula:

$$R_2P\text{-}E\text{-}PR_2 \tag{1}$$

where E stands for a bridge group and R stands for the same or different organic groups, the bond between the organic bridge group and the phosphorus atom being a phosphorous-carbon bond.

Such a ligand is described in WO-A-87,07,600. According to this publication such a ligand, for example 2,2'-bis(diphenylphosphinomethyl)-1,1'-biphenyl (BISBI), is particularly suitable for use in the hydroformylation of unsaturated organic compounds, catalysed with the aid of a transition metal compound based on rhodium. When use is made of the BISBI ligand in combination with a rhodium compound, in the hydroformylation of 1-octene, we have found that the selectivity to normal $C_9$ aldehydes proves to lie around 70–75% and the molar normal/iso ratio of the $C_9$ aldehydes formed decreases from 15 to 4 at increasing degree of conversion. The molar normal/iso ratio (n/iso ratio) is here and hereafter to be understood as the molar ratio of linear aldehydes and branched aldehydes.

A drawback of the state of the art is that a considerable amount of by-products is formed when using the above mentioned ligands. The proportion of by-products (e.g. due to isomerisation), expressed as a percentage of the amount of converted 1-octene, is over 10%.

For many applications a high n/iso ratio is desired in addition to a high aldehyde selectivity.

SUMMARY AND OBJECTS OF THE INVENTION

The aim of the invention is to provide a ligand with which, in combination with a transition metal compound, the catalytic hydroformylation of unsaturated organic compounds is possible with a high selectivity towards aldehydes and thus less by-products are formed.

This aim is achieved in that to the bridge group of the bidentate phosphine ligand consists of an ortho-anellated annular system comprising two aryl groups, which aryl groups are connected by two bridges, a first bridge (bridge 1) consisting of an —O— or an —S— atom and a second bridge (bridge 2) being a group that contains an oxygen, sulphur, nitrogen, silicon or carbon atom or a combination of these atoms, the phosphorus atoms being connected to the two aryl groups of the bridge group at the ortho position relative to the —O— or —S— atom of the first bridge.

It has been found that when the ligand according to the invention is used in combination with a rhodium compound in the hydroformylation of unsaturated organic compounds, 50% less by-products are formed than when a ligand according to WO-A-8707600 is used. An additional advantage is that the n/iso ratio of the aldehydes formed is higher, especially when terminally unsaturated organic compounds are used as the starting material. A further advantage is that the ligands according to the invention are considerably more stable in air (or oxygen) than the ligands according to WO-A-8707600.

Another advantage of the ligand according to the invention is that it can not only be used as part of a catalyst system for a hydroformylation reaction but also as part of a catalyst system for other catalytic processes like e.g. hydrogenation, hydrocyanation, polymerisation, isomerisation, carbonylation, cross-coupling and metathese. The ligand according to the invention will generally form the catalyst system in combination with a catalytically active metal. It has been found that the ligand according to the invention is particularly suitable for use as catalyst system in the hydroformylation of unsaturated organic compounds in combination with a transition metal compound, the metal of which is for example rhodium, ruthenium, cobalt, palladium or platinum. Of the transition metals mentioned, rhodium is a particularly preferred metal.

DETAILED DESCRIPTION OF INVENTION

The aryl groups in the bridge group generally contain between 6 and 14 carbon atoms and may each individually consist of a single-ring structure, whether or not substituted, or of an anellated structure of 2 or more condensed rings, like

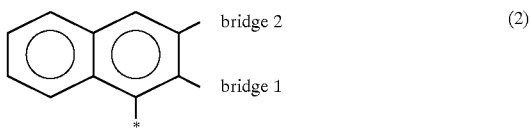

Preferably, the aryl groups have the following structure

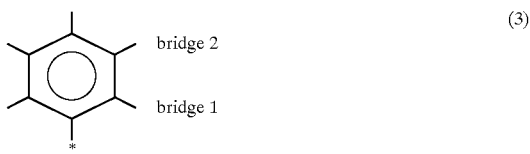

where the phosphorus atom of the phosphine is bound to the aryl group at the ortho-position relative to the first bridge (* in formula 2 and 3) and the aryl group(s) may or may not be substituted.

The second bridge in the bidentate phosphine ligand generally contains an —O—, —S—, —N($R^1$)—, —N$^+$($R^2$)($R^3$)—, —Si($R^4$)($R^5$)—, —P(O)($R^6$)—, —C($R^7$)($R^8$)— group, or a combination of a —C($R^7$)($R^8$)-group with one of the groups mentioned, $R^1$ being a hydrogen atom or an organic group having between 1 and 20 carbon atoms or a polymer, $R^2$ and $R^3$ being organic groups, which may or may not be the same, having between 1 and 20 carbon atoms or a polymer, $R^4$ and $R^5$ being organic groups, which may or may not be the same, having between 1 and 10 carbon atoms, $R^6$ being a hydroxide group or an organic group having between 1 and 10 carbon atoms and $R^7$ and $R^8$ being organic groups, which may or may not be the same, having between 1 and 10 carbon atoms.

The bidentate phosphine ligand according to the invention may for example have a structure according to formula (4):

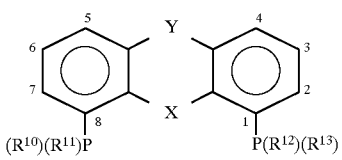

(4)

where X stands for the first bridge and Y for the second bridge, and where $R^{10}$, $R^{11}$, $R^{12}$ and $R^{13}$ stand for organic groups, which may or may not be the same, having between 1 and 14 carbon atoms.

X is preferably an —O— atom. Y is preferably not an —O— atom if X stands for an —O— atom because such ligands are easier to prepare.

$R^1$ in the —N($R^1$)— group may be a hydrogen atom or an organic group having between 1 and 20 carbon atoms or a polymer. If $R^1$ is an organic group, $R^1$ is preferably an aralkyl group, for example benzyl, or an alkyl group, for example a methyl, ethyl, propyl, isopropyl, n-butyl or isobutyl group. $R^1$ may also be an alkylidene group having between 2 and 20 carbon atoms, with which the ligand can be connected to a solid carrier for example silica or a polymer, for example polyethylene. $R^1$ may be a polymer that serves as a carrier.

$R^2$ and $R^3$ in the —N$^+$($R^2$)($R^3$)— group are organic groups, which may or may not be the same, having between 1 and 20 carbon atoms. Examples of possible groups are aralkyl groups, for example benzyl, and alkyl groups, for example a methyl, ethyl, propyl, isopropyl, n-butyl or isobutyl group. $R^2$ and/or $R^3$ may also be an alkylidene group having between 2 and 20 carbon atoms, with which the ligand can be connected to a solid carrier for example silica or a polymer, for example polystyrene. $R^2$ and/or $R^3$ may also be a polymer that serves as a carrier.

The —N$^+$($R^2$)($R^3$)— group may be used with advantage because a bidentate phosphine ligand comprising such a bridge 2 is better soluble in water. This is of use in processes in which the catalyst system is separated using an aqueous medium from an organic reaction mixture. In general, the choice of the anionic counter ion is not critical. If the bidentate phosphine ligand is used in a catalyst, for example in the hydroformylation, use is generally made of an anionic counter ion that does not adversely affect the reaction. Examples of anionic counter ions are $R^{16}$—SO$_3^-$, $R^{16}$—CO$_2^-$ and $R^{16}$—PO$_3^{2-}$, where $R^{16}$ stands for hydrogen or an alkyl group having between 1 and 12 carbon atoms or an aralkyl, alkaryl or aryl group having between 6 and 12 carbon atoms, for example a methyl, ethyl, propyl, isopropyl, n-butyl, isobutyl, phenyl or benzyl group.

$R^4$ and $R^5$ in the —Si($R^4$)($R^5$) group are organic groups, which may or may not be the same, having between 1 and 10 carbon atoms. Examples of possible organic groups are alkyl, aralkyl, alkaryl and aryl groups. Examples of such groups are methyl, ethyl, propyl, isopropyl, n-butyl, isobutyl, phenyl and benzyl groups. $R^4$ and $R^5$ can together form a ring having between 2 and 6 carbon atoms.

$R^6$ in the —P(O)($R^6$)— group is a hydroxide group or an organic group having between 1 and 10 carbon atoms, for example an aryl, alkyl, aryloxy or alkoxy group. Examples of these groups are the phenyl, benzyl, methyl, ethyl, naphthyl, phenoxy, cyclohexyloxy and 2-tert-butylphenoxy groups.

$R^7$ and $R^8$ in the —C($R^7$)($R^8$)— group independently of one another stand for organic groups having between 1 and 10 carbon atoms. Examples of possible organic groups are the methyl, ethyl, propyl, isopropyl, butyl, isobutyl and the phenyl groups. $R^7$ and $R^8$ may together form a ring having between 2 and 6 carbon atoms.

$R^{10}$, $R^{11}$, $R^{12}$ and $R^{13}$ may independently of one another be an alkyl, aryl, aralkyl, alkaryl or a cycloaliphatic group having between 1 and 14 carbon atoms, which may or may not be substituted. Preferably these groups are cycloalkyl or aryl groups having between 5 (or 6 in the case of aryl groups) and 14 carbon atoms. Most preferably these groups are phenyl, naphthyl, diphenyl or cyclohexyl groups.

The aryl groups in the bridge group and the aryl, aralkyl, alkaryl or cycloalkyl groups $R^{10}$, $R^{11}$, $R^{12}$ and $R^{13}$ may be substituted with organic groups containing between 1 and 10 carbon atoms, or with other groups, for example halogen groups or groups that increase the bidentate phosphine ligand's solubility in water. Possible organic groups are alkyl groups, for example the methyl, ethyl, propyl, isopropyl, butyl, isobutyl and pentyl groups; alkoxy groups, for example the methoxy and ethoxy groups; cycloaliphatic groups, for example cyclopentyl, cyclohexyl; alkanoyl, for example acetyl, benzoyl; halogen groups, for example fluorine and chlorine; halogenated alkyl groups, for example —CF$_3$; and ester groups, for example acetic esters. When $R^{10}$, $R^{11}$, $R^{12}$ or $R^{13}$ is a phenyl group, then alkoxy groups, alkyl groups, halogens and halogenated alkyl groups may with advantage be ortho- and para-substituted to the phenyl group.

Examples of substituents that increase the bidentate phosphine ligand's solubility in water are the carboxylate group, —COOM, the sulphonate group, the —SO$_3$M, phosphate group, the —PO$_3$M$_2$ and the ammonium salt —N($R^{14}$)$_3$A.

Suitable cations M are inorganic cations of metals, in particular of alkali and alkaline earth metals for example sodium, potassium, calcium or barium, and also ammonium ions or quaternary ammonium ions, for example tetramethyl ammonium, tetrapropyl ammonium or tetrabutyl ammonium.

Suitable anions A are sulphate and phosphate groups and organic acid groups for example $R^{15}$—SO$_3^-$, $R^{15}$—CO$_2^-$ and $R^{15}$—PO$_3^{2-}$, where $R^{15}$ may be an organic group having between 1 and 18 carbon atoms. Examples of suitable organic groups are alkyl, aralkyl, alkaryl and aryl groups.

Suitable $R^{14}$ and $R^{15}$ groups are aliphatic hydrocarbon groups having between 1 and 18 carbon atoms, for example the methyl, ethyl, n-butyl, isobutyl and pentyl groups.

Examples of bidentate phosphine ligands according to the invention are ligands 1 up to and including 31, in which Ph represents a phenyl group, a dash a methyl group and -Et an ethyl group.

Ligands 1–31 are represented hereinbelow:

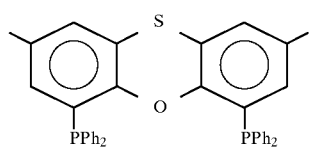

Ligand 1

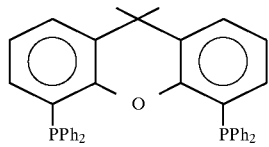

Ligand 2

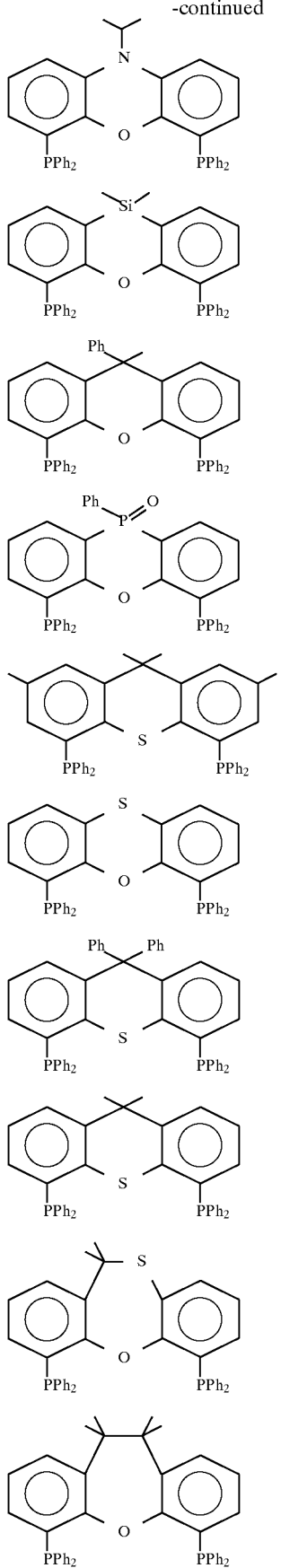
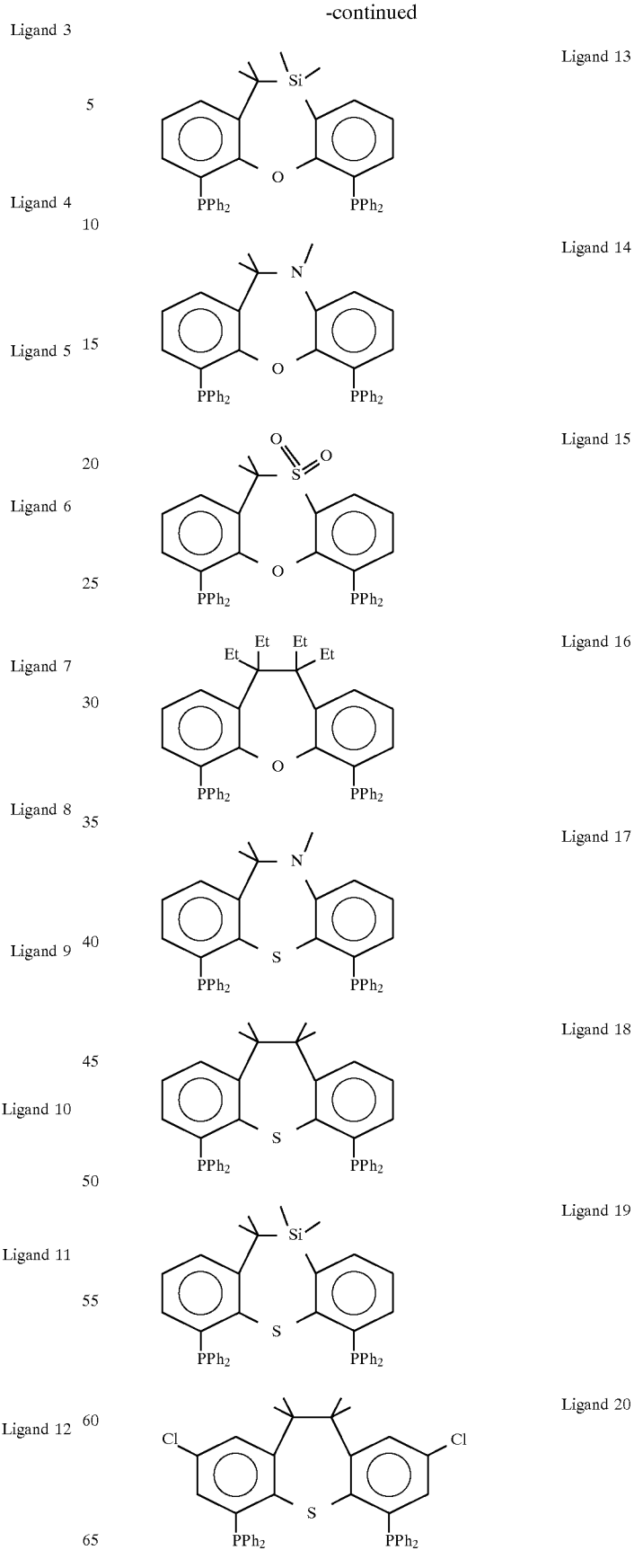

-continued

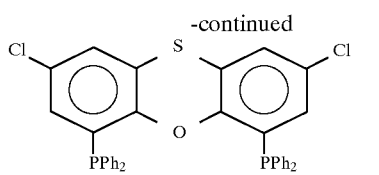
Ligand 21

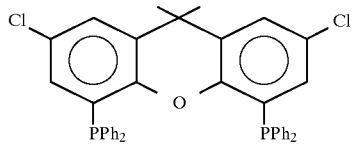
Ligand 22

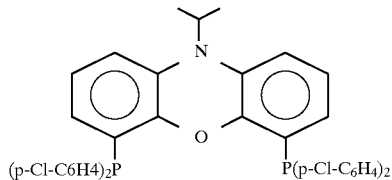
Ligand 23

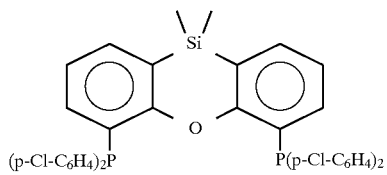
Ligand 24

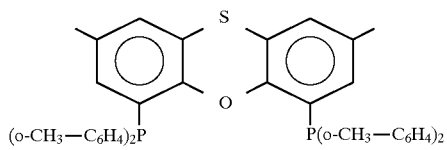
Ligand 25

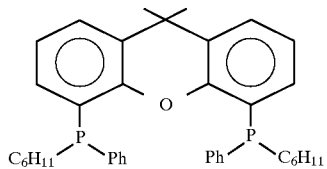
Ligand 26

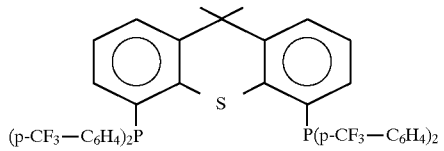
Ligand 27

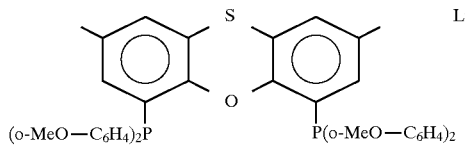
Ligand 28

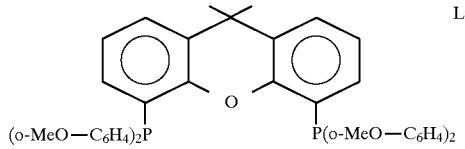
Ligand 29

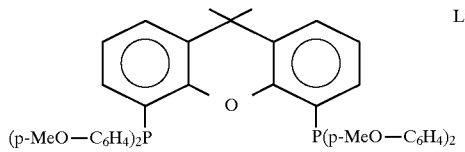
Ligand 30

-continued

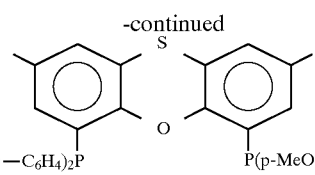
Ligand 31

The invention also relates to a method for the preparation of a bidentate phosphine ligand according to the invention. The ligand according to the invention can be prepared using methods that are, in itself, available to a person skilled in the art. The bidentate phosphine ligand can be prepared in a manner similar to that described by M. W. Haenel, et al., Chem. Ber. 125 (1991) 1705–1710. In such a preparation of the ligand an organic compound, which corresponds to the bridge group of the ligand (having hydrogen atoms at the position at which the bonds to the phosphorus atoms will ultimately be), is dissolved in a mixture of a suitable solvent, together with a strong base and an additional complexing agent, after which 2 or more equivalents of an organic phosphorous compound, optionally dissolved in a solvent, are added to the mixture, in which process the bidentate phosphine ligand is formed. The ligand according to the invention can for example with advantage be prepared by dissolving a compound which is the same as the bridge group of the ultimate ligand (i.e. without the phosphorus atoms), in a suitable solvent. Suitable solvents are for example ether, for example diethyl ether, tetrahydrofuran or dioxane, or an aliphatic hydrocarbon, for example hexane or cyclohexane, or a mixture of these solvents. Subsequently a strong base is added to this solution, for example n-BuLi (BuLi=butyl lithium), s-BuLi or t-BuLi. Other strong bases based on K, Na and Mg are also suitable for this purpose. The strong base is generally added at a low temperature, for example of between −80° and 0° C., after which the temperature of the mixture is slowly increased to for example room temperature. It is advantageous to add an extra complexing agent for the strong base, for example tetramethylethylene diamine or tetramethylurea. This complexing agent for the strong base may be added before or after the addition of the base. The mixture thus obtained is mixed for a certain period of time (generally between 10 and 20 hours) at a temperature that is generally between −80° and 80° C., in the process of which a 1,8-bis-metallised compound is formed. Then the solution is again cooled to a temperature of between −80° and 0° C. A mixture containing 2 or more equivalents of $Ar_2PZ$ (Ar corresponding to the ultimate $R^{10}$, $R^{11}$, $R^{12}$ and $R^{13}$ groups, Z standing for a halogen atom or an alkoxy group having between 1 and 4 carbon atoms; suitable halogen atoms being Cl, Br and I) and optionally a solvent, for example hexane or tetrahydrofuran, is then added. After some time, for example 10–20 hours' stirring at for example room temperature, the reaction mixture is further extracted with an aqueous solution and dried. The product may be for example purified through crystallisation.

The invention also relates to a catalyst system comprising a bidentate phosphine ligand and a transition metal compound in which the bidentate phosphine ligand is a ligand according to the invention.

The bidentate phosphine ligand/transition metal compound ratio is generally between 0.5 and 100. Preferably this ratio is between 0.5 and 10. The ratio chosen proves to have little effect on the selectivity towards aldehydes, but for practical reasons, for example the solubility of the ligand and the transition metal compound cost price, it will usually lie within the aforementioned limits.

For hydroformylation reactions the transition metal compound is preferably based on a rhodium compound. Such a catalyst system can be prepared by dissolving the bidentate phosphine ligand and a rhodium compound in a solvent or in the reaction mixture. Examples of rhodium compounds that can be used are $Rh(CO)_2(t-C_4H_9\text{—}COCHCO-t-C_4H_9)$, $Rh(CO)_2(acac)$ (acac=acetylacetonate), $Rh_2O_3$, $Rh_4(CO)_{12}$, $Rh_6(CO)_{16}$, $[Rh(OAc)_2]_2$ (OAc=acid residue of acetic acid) and rhodium (ethylhexanoate)$_2$. Preferably, $Rh(CO)_2(acac)$ or $[Rh(OAc)_2]_2$ is used as the rhodium compound because these compounds can be easily obtained.

The invention also relates to a method for the preparation of an aldehyde through hydroformylation, using an ethylenically unsaturated organic compound as a starting material, in the presence of carbon monoxide, hydrogen and a catalyst system according to the invention. Preferably the transition metal compound is a rhodium compound.

Unsaturated compounds that can be hydroformylated to aldehydes using the method according to the invention are for example linear and branched unsaturated organic compounds having between 2 and 20 carbon atoms. The organic compounds may optionally contain functional groups. Examples of such functionalized unsaturated organic compounds are unsaturated carboxylic acids, esters, amides, acrylamides, nitriles, aldehydes, ketones, alcohols and ethers.

The organic compounds may be for example alkenes, for example ethylene, propylene, 1-butylene, 2-methylpropylene, 2-methyl-1-butylene, 1-pentene, 1-hexene, 1-heptene, 1-octene, 2-ethyl-1-hexene, 1-dodecene, 1-octadecene, 1,5-hexadiene, 1,7-octadiene, 1,9-decadiene, 1,3-butadiene, isoprene, 1,3-pentadiene, 1,4-pentadiene, vinyl cyclohexene; aromatic compounds with one or more aliphatic unsaturated substituents, for example styrene; unsaturated esters, for example vinyl acetate, alkyl acetate, alkyl propionate; alkyl acrylates, for example methyl methacrylate, methyl acrylate, ethyl acrylate; unsaturated aldehydes for example acroleine, unsaturated carboxylic acids, for example 3-pentenoic acid and 4-pentenoic acid; pentenoates, for example methyl-4-pentenoate, methyl-3-pentenoate; unsaturated ethers, for example allyl ethers, for example allyl ethylether; vinyl ethers, for example vinyl methylether, allyl ethylether; styryl ethers, for example styryl methylether or styryl silylether; unsaturated acetals, for example the acetal of 4-pentenal and ethylene glycol; alkenols, for example allyl alcohol and 2,7-octadienol; unsaturated nitriles, for example 3- and 4-pentene nitrile; unsaturated amides, for example 5-hexene amide and alkyl acrylamides; unsaturated silanes, for example vinyl silane; unsaturated siloxanes, for example vinyl siloxane.

The method according to the invention can also be used to convert unsaturated polymers into polymers with aldehyde groups. An example of such an unsaturated polymer is 1,2-polybutadiene.

The method according to the invention is suitable for the preparation of aldehydes in which a high selectivity towards the total of aldehydes is obtained. If it is not important which aldehyde functionality is ultimately formed (normal or iso), this method can with advantage be used for all the substrates mentioned above. If it is important that the aldehyde functionality is with a very high selectivity to be at the end of a carbon chain (i.e. high n/i ratio), use is preferably made of terminally unsaturated organic compounds (the unsaturation being at the end of the molecule's carbon chain), a number of which have been mentioned as examples above. It has also been found that the reaction rate is highest when use is made of these terminally unsaturated organic compounds.

The reaction conditions under which the hydroformylation according to the invention can be carried out will be described below.

The temperature may be between 30° and 150° C. More preferably, the temperature is between 50° and 120° C. The pressure may be between 0.1 and 60 MPa. More preferably, the pressure is between 0.3 and 30 MPa, most preferably between 0.5 and 6 MPa.

The molar ratio of the hydrogen to carbon monoxide, added to the reaction zone or present during the reaction, may depend on the substrate and the chosen reaction conditions in a commonly known manner. The hydrogen/carbon monoxide molar ratio is generally between 0.5 and 4.0 during the hydroformylation. In some cases, however, the yield of desired product and also the reaction rate can be increased by choosing a ratio higher than 4.0. During the hydroformylation the total molar amount of carbon monoxide and hydrogen is generally 0.01 to 20 times the molar amount of unsaturated organic compound (substrate). More preferably this ratio is between 1.2 and 6.

The hydroformylation is generally carried out in the presence of a solvent. If so desired, the hydroformylation may however also be carried out without a solvent.

Organic solvents that are inert or do not interfere with the hydroformylation are suitable solvents. Examples of suitable solvents are the starting compound and the reaction product and compounds related to the product to be formed, for example by-products and in particular condensation products. Other suitable solvents are saturated hydrocarbons for example naphthas, kerosine, mineral oil and cyclohexane, and aromatic hydrocarbons, ethers, ketones, nitrites, amides and urea derivatives, for example toluene, benzene, xylene, Texanol® (Union Carbide), diphenylether, tetrahydrofuran, cyclohexanone, benzonitrile, N-methylpyrrolidone and N',N'-dimethylethylurea. The solvent and substrate are preferably free of catalyst poisons known for the hydroformylation, for example acetylene, butadiene, 1,2-propadiene, thiophenol, dialkyldisulphide or HCl.

If a rhodium compound is used as transition metal compound in the catalyst system, the amount of rhodium in the reaction mixture may vary from $1*10^{-6}$ to 0.1 mol of rhodium per mol of substrate. Low rhodium concentrations are however not attractive from a commercial point of view because then the reaction rate is not high enough. The upper limit is determined by rhodium's high raw material price. In principle there is no objection to choosing a rhodium concentration of above 0.1 mol per mol of substrate. However, this concentration is generally between $1*10^{-5}$ and $5*10^{-2}$ mol of Rh per mol of substrate. Preferably this concentration is between $1*10^{-4}$ and $1*10^{-2}$ mol of Rh per mol of substrate.

The residence times can vary considerably and depends on the desired degree of conversion, yield and/or selectivity of the reaction.

The hydroformylation may be carried out both batchwise as well as in continuous mode. The hydroformylation is generally carried out in continuous mode. The hydroformylation can for example be carried out in a so-called bubble reactor, liquid-overflow reactor, continuously stirred tank reactor or a trickle bed.

The invention also relates to a process for the preparation of esters by carbonylation of an unsaturated compound in the liquid phase in the presence of an alkanol, carbon monoxide, a bidentate ligand of the invention and a transition metal compound.

The unsaturated compound may be of the type described previously as substrate for hydroformylation reactions.

The alkanol as a rule has 1–20 carbon atoms. The alkanol may be an aliphatic, cycloaliphatic or aromatic compound. Examples of suitable alkanols are methanol, ethanol, propanol, cyclohexanol, phenol. The quantity of alkanol applied is not critical. Preferably, the molar ratio of alkanol-:unsaturated compound is 1:1.

The metal in the transition metal compound used can be rhodium, ruthenium, palladium, platinum or cobalt; palladium is a preferred metal and a palladium based catalyst and its uses will be described below.

The actual catalyst system is a complex between the transition metal compound and the ligand. In these complexes other ligands next to the ligand according to the invention are used, for example halogen atoms; hydride; carboxylates; CO; solvents, for example acetonitril, ether and the like; nitrogen bases, like pyridine, quinoline and dimethylaniline; olefins for example ethylene; or dienes for example cyclooctadiene; aryl groups bound through all or part of their π-orbitals for example eta-6 benzene, or eta-6 cumene.

Another way to create an active catalyst is by using a catalyst precursor, for example $PdCl_2$, $Pd(OAc)_2$, palladium nitrate, palladium on carbon in conjunction with 1 to 5 equivalents of the ligand of the invention. A more preferred ratio is between 1 and 2.

The ratio of catalyst to substrate can vary in between $10^{-1}$ and $10^{-6}$, but more preferably lies between $10^{-2}$ and $10^{-4}$.

It may also be advantageous to use a cocatalyst for example $SnCl_2$, in a ratio of 1–5 equivalents with respect to the transition metal, to enhance the reactivity of the catalyst. If palladium is used as the transition metal the carbonylation is preferably carried out in the presence of a catalytic quantity of a protonic acid. The pKa of the acid is dependant upon the type of unsaturated substrate. For conjugated substrates like 1,3-butadiene a protonic acid with pKa>3 (measured in water at 18° C.) is used. Examples are benzoic acids preferably trimethylbenzoic acid and valeric acid. With non conjugated alkenes as substrates an acid with pKa<3 (measured in water at 18° C.) like a sulfonic acid is used.

All inert solvents are in principle suitable as additional solvent, but it is also possible to use an excess amount of one of the reactants, products or side products in such an amount that a suitable liquid phase is obtained. Examples of suitable solvents are sulfolane, toluene, esters, diphenyl ether and the like. If 1,3-butadiene is used as the unsaturated substrate, methyl valerate or pentenoate esters can be used advantageously as solvent.

The carbonylation is preferably carried out at CO pressures between 2 and 30 MPa, and more preferably between 5 and 20 MPa; the temperatures can range between 20° and 200° C., but more preferred are temperatures between 50° and 150° C.

The products of the above described carbonylation reaction are esters. If butadiene is used as a substrate a mixture of pentenoic esters, containing mostly 3-pentenoic ester, will be obtained. However it is also possible by tuning of the reaction conditions like temperature and CO pressure to carbonylate 3-pentenoic ester or a mixture of pentenoic esters to obtain a mixture of diesters in which adipic ester is found the most abundantly. In a similar way it is possible to carbonylate 3-penteno-1-nitrile to obtain a mixture of nitrile esters in which 5-cyanopentanoic ester is the main product. Also, 3-pentenoic acid may be carbonylated to give a mixture of acid esters in which the adipic mono ester is the main product.

If in the carbonylation reaction described above, using the palladium based catalyst, the alkanol is replaced by water the product will be a carboxylic acid. In this case butadiene will give a mixture of pentenoic acids, containing mostly 3-pentenoic acid. Carbonylation of 3-pentenoic acid or mixtures of pentenoic acids will give rise to a mixture of di-acids containing mostly adipic acid.

If in the carbonylation reaction described above, using the palladium based catalyst, the alkanol is replaced by an amine, the product will be an amide.

If in the carbonylation reaction described above, using the palladium based catalyst, the alkanol is replaced by a thiol, the product will be a thioester.

The invention also relates to a process for transition metal catalyzed hydrocyanation reactions of olefins, polyenes and acetylenes to give nitriles. Whereas the state of the art of transition metal catalyzed hydrocyanation clearly prefers phosphite ligands or ligands containing at least one POR bond (where R is an aryl or alkyl group) for the hydrocyanation of olefins, and whereas only highly reactive (strained) olefins like norbornene and norbornadiene can be hydrocyanated in good yield using conventional bisphosphine ligands, the ligands of the invention can be used for the hydrocyanation of all olefins, for example 1-octene and styrene. Whereas phosphite ligands are easily hydrolysed by water the ligands of the invention are stable both in storage as well as during the use in the hydrocyanation reaction.

The conventional hydrocyanation catalysts, based on nickel in its zero-valent state in conjunction with phosphite ligands, suffers from oxidation by hydrogen cyanide (HCN), leading to the irreversible formation of $Ni(CN)_2$ complexes which are catalytically inactive. This can be countered by performing the hydrocyanation reaction with low concentrations of HCN, but this has an adverse effect on the productivity of the reaction. The ligands of the invention form active catalysts with Nickel(0) that show a remarkable resistance against oxidation by HCN and remain active till the end of the reaction. This allows the use of high concentrations of HCN leading to higher productivity per unit of space and unit of time.

Several transition metals can serve to form active hydrocyanation catalysts with the ligands of the invention, for example Ni(0), Pd(0), Pt(0), Co(0) or Co(I), Fe(0), Rh(I), Ru(II), Ir(I), Mo(0) or W(0). Of these Ni(0) is the most preferred metal. Several methods are available to form complexes of these metals with the ligands of the invention. These complexes can be used as catalyst. However, it is also possible to use a catalyst precursor for example $Ni(COD)_2$ (COD=cyclooctadiene) or $Pd(DBA)_2$ (DBA=dibenzylideneacetone), in combination with the ligands of the invention.

The ratio between ligand and metal may vary, the optimal ratio being different for each metal, but will usually lie between 1 and 5 and more preferred between 1 and 2. The catalyst can be used in ratios with respect to the amount of substrate varying in between $10^{-1}$ and $10^{-6}$ mol%, but more preferred in between $5.10^{-2}$ and $10^{-4}$ mol%.

A Lewis acid co-catalyst may be used in combination with the catalysts described above, but the hydrocyanation reaction can also be performed in the absence of these co-catalysts. Many Lewis acids are suitable, for instance $ZnCl_2$, $AlCl_3$, $Ph_3B$ or $AlEtCl_2$.

The olefinic substrates used in the hydrocyanation may be terminal olefins, for example ethylene, propylene or 1-butene, but also internal olefins, for example 2-octene; also a mixture of olefins may be hydrocyanated, to give terminal nitriles preferentially. The olefins may carry a variety of substituents: 3-pentenenitrile or mixtures of isomeric pentenenitrile may be hydrocyanated to give dicyanobutanes, containing mostly adiponitrile. 3-pentenoic acids and their esters or isomeric mixtures thereof can be hydrocyanated to give cyanopentanoic acids or the esters, respectively. The linear products are predominant in the product mixtures.

Cyclic olefins like cyclohexene may also be hydrocyanated. Aromatic olefins, for example styrene may be hydrocyanated with these catalysts giving nitriles with extremely high iso to normal ratios.

Dienes or polyenes are also excellent substrates for the hydrocyanation reaction. For instance butadiene may be hydrocyanated to give a mixture of pentenenitrile containing mostly 3-pentenenitrile.

Acetylenic substrates like acetylene, propyne or 1-hexyne may be hydrocyanated with the catalysts of the invention to give olefinically unsaturated nitriles.

The HCN may be administered to the reaction mixture in liquid form, as a solution in an organic solvent, for example toluene, or as a gas sparged through the solution, or blown over the surface of the solution of the catalyst and the substrate.

Solvents that can be used are toluene, ethyl acetate, methyl tert-butyl ether, acetonitrile, sulfolane, diphenyl ether and the like, but the reaction can also conveniently be carried out without a solvent or with the substrate, the product or side products as solvent.

The reaction may be carried out at temperatures between $-40°$ C. and $120°$ C., but more conveniently between $0°$ C. and $100°$ C.

There are many ways in which these hydrocyanation reactions can be conveniently carried out. These have been described in detail in the abundantly available literature. A number of examples are presented in the experimental section.

The ligands of the invention can also be used in combination with transition metals for the hydrogenation of olefins, dienes, alkynes, aldehydes, ketones and imines. Several transition metals may be used, for example Rh, Ru, Ir, Co, Ni, Pd, Pt, Fe, Cr, W and Os. The catalyst may consist of a preformed complex of the metal with the ligand. In these complexes the metals may carry other ligands, for example halogen atoms; hydride; carboxylates; CO; solvents, for example acetonitril, ether and the like; nitrogen bases, like pyridine, quinoline and dimethylaniline; olefins for example ethene; or dienes for example cyclooctadiene; aryl groups bound through all or part of their $\pi$-orbitals for example eta-6 benzene, or eta-6 cumene. The complexes may be positively or negatively charged, or even carry more than a single charge. In this case the complex will have a counter anion for example a halide ion, a tosylate, a carboxylate, a composite anion, for example $BF_4^-$, $PF_6$, $B(C_6F_5)_4$, in case of a cationic complex, and a countercation, for example $Na^+$, $K^+$, $Ca^{2+}$, in case of an anionic complex. It might also be advantageous to treat a complex of the transition metal and the ligand of the invention, which may contain other ligands, with bases, for example aqueous NaOH, or aqueous bicarbonate. It may also be advantageous to use as catalyst a reduced form of said complex, which can be prepared by treating the complex with a reducing agent, for example $NaBH_4$, $LiAlH_4$, Zn powder, $H_2$, alcohols, trialkyl-amines, and the like.

It may also be advantageous to use a catalyst precursor for example $[Rh(COD)Cl]_2$ or $Pd(DBA)_2$ in conjunction with the ligand of the invention.

The ratio between catalyst and substrate in general varies in between $10^{-1}$ and $10^{-6}$, but will usually lie between $2.10^{-2}$ and $5.10^{-5}$.

The hydrogenation is carried out with hydrogen at pressures between 0.01 and 100 MPa, but more usually will be carried out at pressures between 0.1 and 10 MPa. The hydrogenation can also take the form of a transfer hydrogenation. In this case no hydrogen gas is used but hydrogen is transferred from a reducing agent, for example secondary alcohols, like isopropanol; aromatic alcohols like benzyl alcohol; formic acid or salts thereof; or hypophosphorous acid or salts thereof.

The hydrogenation can be performed in a solvent or carried out in the absence of solvent; in this case the starting material and/or the product will be the solvent.

The ligands of the invention can also conveniently be used in conjunction with a variety of transition metals as catalysts for the isomerisation of olefins, dienes, polyenes, alkynes; allyl ethers are converted to enol ethers, allyl amines to enamines, allyl amides to enamides, allyl alcohols to ketones, and epoxides to aldehydes and/or ketones. Isomerisation processes in a general sense have been described extensively in Penny Chaloner, "Handbook of Coordination Catalysis in Organic Chemistry". From this article it becomes clear what the expected products of these isomerisation reactions are and what the scope is of these isomerisation reactions. The ligands of the invention can be advantageously used because they form stable complexes which give high turnover numbers in these reactions. Turnover number here and hereinafter are to be understood as being the number of substrate molecules that can be converted per molecule of transition metal compound.

Suitable transition metals are V, Nb, Ta, Cr, Mo, W, Fe, Ru, Os, Co, Rh, Ir, Ni, Pd, Pt, and Cu. The catalysts may take the form of a complex between the transition metal and the ligand like described above for the hydrogenation catalysts, or may be prepared in situ from a suitable catalyst precursor and the ligand. It may be advantageous to add an acid like acetic acid, p-toluenesulfonic acid, trifluoroacetic acid, HCl, silica aluminum oxide (neutral or acidic), or an acidic ion exchange resin, and the like to the reaction mixture to enhance or even enable the isomerisation activity. It might also be advantageous to treat a complex of the transition metal and the catalyst, which may contain other ligands, with bases, for example aqueous NaOH, or aqueous bicarbonate and use the resulting compound as catalyst. It may also be advantageous to use as catalyst a reduced form of said complex, which can be prepared by treating the complex with a reducing agent for example $NaBH_4$, $LiAlH_4$, Zn powder, $H_2$, alcohols, trialkyl-amines, and the like.

The ligands of the invention can also be used conveniently in transition metal catalysed cross coupling reactions. In these reactions a compound possessing a leaving group on an $sp_2$-carbon atom, for example aryl halides, aryl triflates, aryl sulfonates, vinyl halides, vinyl triflates and vinyl sulfonates is coupled with a nucleophile for example a Grignard reagent, an alkyllithium compound, an alkylated zinc compound, an alkyl aluminum compound, an alkyl- or aryl boronic acid or ester thereof, and other C-nucleophiles for example cyanide anion.

Suitable transition metals are Fe, Co, Ni, Pd and Cu. Of these Ni and Pd are preferred metals. Nickel is especially preferred.

The actual catalyst can be a preformed complex between the transition metal and the ligand of the invention as described above or may be prepared in situ from a catalyst precursor. Reaction between $PdCl_2$ and a ligand of the invention in a 1:1 ratio will give the complex $PdCl_2$(Ligand). Likewise $NiCl_2$ gives $NiCl_2$(Ligand).

The catalyst/substrate ratio in general varies between $10^{-1}$ and $10^{-5}$, but more preferred is a ratio between $10^{-2}$ and $5.10^{-4}$.

The solvent used is dependant on the type of nucleophile. Ether type solvents are best used in conjunction with Grignards and alkyllithium compounds, but other nucleophiles can tolerate a wider range of solvents.

The preferred temperature is also dependant upon the type of nucleophile. Grignards and alkyllithium compounds can be used at temperatures between −30° and 50° C., but other nucleophiles are more tolerant of higher temperatures.

The invention will be elucidated with reference to the following non-limiting examples.

EXAMPLE I
Preparation of 4a-10a-dihydro-2,8-dimethyl-4,6-bis(diphenylphosphine) phenoxathiine (Ligand 1; formula sheet)

30.3 ml of s-BuLi (1.3M in 98/2 (vol/vol) cyclohexane/hexane, 39.4 mmol), was added dropwise, at −60° C., to a stirred solution of 3.0 g of dimethylphenoxathiine (13.1 mmol), 4.6 ml of TMEDE (N,N,N',N'-tetramethyl-1,2-diaminoethane) (39.4 mmol) and 250 ml of dry diethyl ether.

After all the s-BuLi had been added, the cooling bath was removed to enable the solution to reach room temperature. After 16 hours the mixture was then cooled to −60° C., after which a solution of 8.7 ml (48.5 mmol) of chlorodiphenylphosphine in 40 ml of hexane was added dropwise. The cooling bath was again removed and the reaction mixture was stirred for 16 hours. The ether was removed at reduced pressure (vacuum) and the remaining oil was dissolved in $CH_2Cl_2$, then washed with water, dried under $N_2$ with the aid of $MgSO_4$ and the solvent was removed in a vacuum. The residue thus obtained was washed with hexane and crystallised from 1-propanol. The white crystals obtained proved to be stable in the presence of air. The yield was 71%. The crystals were analysed. The NMR spectra were recorded with the aid of a Bruker AMX-300 FT-NMR, the IR spectra with the aid of a Nicolet 510 FT-IR. The results were:

$^1$H-NMR (300 MHz, CDCl$_3$) δ: 7.16–7.35 (Ar, 20 H) P(C$_6$H$_6$), 6.87("d", J=1.6 Hz, C(P(Ph)$_2$)—CH—C(CH$_3$)), 6.23(bs,2H,C(S)—CH—C(CH$_3$)), 2.07(s,6H,CH$_3$).
$^{31}$P-NMR (121.5 MHz,CDCl$_3$) δ: −17.34.
IR:(CHCl$_3$,cm$^{-1}$):3004(m)2961(m),2926(m),1435(s), 1407(vs), 1244(m), 695(m).

EXAMPLE II
Preparation of 4a,9a-dihydro-9,9-dimethyl-4,5-bis(diphenylphosphino) xanthene (Ligand 2; formula sheet)

11 ml of s-BuLi (1.3M in 98/2 (vol/vol) cyclohexane/hexane, 14.3 mmol) was added dropwise, at room temperature, to a stirred solution of 1.0 g of 9,9-dimethylxanthene (4.8 mmol) and 2.3 ml of TMEDE (14.3 mmol) and 50 ml of dry diethyl ether. The reaction mixture was stirred for 16 hours.

Then the mixture was cooled to 0° C. and a solution of 2.6 ml of chlorodiphenylphosphine (14.3 mol) in 5 ml of tetrahydrofuran was added dropwise. A suspension was formed. This mixture was stirred for 4 hours. The solvent was removed at reduced pressure and the resulting oil was dissolved in 40 ml of $CH_2Cl_2$, then washed with 15 ml of water, dried with the aid of $MgSO_4$. After that the solvent was removed under a vacuum. The resultant sticky mass was washed with hexane and crystallised from 1-propanol, after which a powder was obtained. The yield was 2.05 g of yellowish white powder (yield 75%). The product proved to be stable in the presence of air in powdered form and also in a CDCl$_3$ solution.

As in Example I, the powder was analysed. $^1$H-NMR(300 MHz,CDCl$_3$) δ: 7.40(dd,2H,J=7.8,1.0 Hz,CP—CH—CH),7.15–7.26(ar,20H)P(C$_6$H$_6$), 6.96(t,2H,J=7.7 Hz,CH—CH—CH),6.54 (dd,2H,J=7.4,1.4 Hz,CH—CH—CC),1.65(s,6H,CH$_3$).
$^{31}$P-NMR (121.5 MHz,CDCl$_3$) δ: −17.52.
IR:(CHCl$_3$,cm$^{-1}$):3073(w),2974(w),1435(s),1405(vs), 1243(m), 695(m).

EXAMPLE III
Hydroformylation of 1-octene with ligand 1 and Rh

A 180-ml stainless steel autoclave with a glass liner was filled with 5 ml of a mixture of 5 mmol Rh(acac)(CO)$_2$ and toluene(25.10$^{-3}$ mmol), 0.0164 g of the ligand of Example I (27.5*10$^{-3}$ mmol), and 3.0 ml of 1-octene. The total volume was 8.6 ml, the Rh/substrate ratio was 1.5*10$^{-3}$. The pressure at the beginning of the reaction was 1.0 MPa (1:1 (mol:mol) CO:H$_2$) and the temperature was 40° C. The reaction was carried out batchwise. No additional carbon monoxide or hydrogen was added during the reaction. The results are shown in Table 1.

EXAMPLE IV–VI
Hydroformylation of 1-octene with ligand 1 and Rh

Example III was repeated using a variable ligand/rhodium (L/Rh) ratio as indicated in Table 1. The results are shown in Table 1.

EXAMPLE VII
Hydroformylation of 1-octene with ligand 1 and Rh

Example III was repeated at 80° C. The results are shown in Table 1.

Comparative Experiment A
Hydroformylation of 1-octene with BISBI and Rh

Example VII was repeated using 2,2'-bis(diphenylphosphinomethyl)-1,1'-biphenyl (BISBI), as the ligand. The results are shown in Table 1.

Comparative Experiment B
Hydroformylation of 1-octene with BISBI and Rh

Example III was repeated using BISBI as the ligand. The results are shown in Table 1.

EXAMPLE VIII
Hydroformylation of 1-octene with ligand 1 and Rh

Example III was repeated at 100° C. The results are shown in Table 1. From the results it can be seen that at a higher temperature the degree of conversion is higher, but the selectivity towards the aldehyde is lower.

TABLE 1

| Example/Experiment | L/Rh | time (hr) | degree of conversion (%) (1) | isomerisation sel. (%) (2) | sel. aldehyde (%) (3) | n/iso (4) | sel. n-aldehyde (%) (5) |
| --- | --- | --- | --- | --- | --- | --- | --- |
| III | 1.1 | 5.17 | 12.5 | 9.6 | 90.4 | 5.7 | 77.0 |
| IV | 2.2 | 22.10 | 31.8 | 6.4 | 93.6 | 44.9 | 91.6 |
| V | 5.0 | 16.0 | 30.3 | 6.7 | 93.3 | 45.1 | 91.3 |
| VI | 10.0 | 19.5 | 34.1 | 5.1 | 94.9 | 45.4 | 92.9 |

TABLE 1-continued

| Example/Experiment | L/Rh | time (hr) | degree of conversion (%) (1) | isomerisation sel. (%) (2) | sel. aldehyde (%) (3) | n/iso (4) | sel. n-aldehyde (%) (5) |
|---|---|---|---|---|---|---|---|
| VII | 2.2 | 1.05 | 67.4 | 7.2 | 92.8 | 53.0 | 91.1 |
|  |  | 10.0 | 98.7 | 4.7 | 95.3 | 41.4 | 93.1 |
| VIII | 2.2 | 0.08 | 38.4 | 15.5 | 84.5 | 33.7 | 82.1 |
|  |  | 0.17 | 55.9 | 14.5 | 85.5 | 44.9 | 83.6 |
|  |  | 0.25 | 72.5 | 14.8 | 85.2 | 38.0 | 83.0 |
| A | 2.2 | 0.17 | 49.8 | 20.8 | 79.2 | 15.8 | 74.5 |
|  |  | 1.25 | 98.3 | 10.7 | 89.3 | 4.1 | 71.8 |
| B | 1.1 | 2.0 | 53.1 | 94.9 | 5.1 | 3.6 | 4.0 |

(1) molar percentage of converted 1-octene
(2) molar selectivity towards internally unsaturated octene (isomerisation to 2-octene)
(3) molar selectivity towards total aldehyde (= normal + iso aldehyde)
(4) n/iso molar ratio
(5) molar selectivity towards n-aldehyde

EXAMPLE IX

Hydroformylation of 1-octene with ligand 2 and Rh

Example III was repeated using the ligand of Example II at 40° C. The results are shown in Table 2.

TABLE 2

| L/Rh | time (hr) | degree of conversion (%)(1) | isomerisation (%)(2) | sel. aldehyde (%)(3) | n/iso (4) | sel. n-aldehyde (%)(5) |
|---|---|---|---|---|---|---|
| 2.2 | 0.08 | 18.8 | 4.0 | 96.0 | 49.9 | 94.1 |
|  | 0.17 | 22.9 | 4.3 | 95.7 | 44.6 | 93.6 |
|  | 0.25 | 34.9 | 7.3 | 92.7 | 50.9 | 90.9 |
|  | 0.45 | 74.2 | 7.2 | 92.8 | 49.4 | 91.0 |

(1)–(5) see legend Table 1.

For all the given results the selectivity towards the total amount of aldehydes is 100% minus the percentage of the 1-octene that has isomerised to internally unsaturated octenes (see Tables 1 and 2). These internally unsaturated octenes are undesired by-products when terminal aldehydes are being prepared, because these octenes are generally not very reactive and, if they do react, they are converted with a high selectivity into the undesired iso aldehyde.

When the results of Example VII and Comparative Experiment A (or Example III and Experiment B) are compared it can be seen that a higher selectivity and yield of total aldehydes and a higher n/i ratio are obtained when use is made of the bidentate phosphine ligand according to the invention than when use is made of the bidentate phosphine ligand according to WO-A-8707600.

EXAMPLE X

Hydroformylation of styrene with ligand 2 and Rh

Example III was repeated using the ligand of Example II in a L/Rh ratio of 2.2 and styrene as substrate. The Rh/substrate ratio was $1.5*10^{-3}$. The amount of Rh used was 1.78 mmol. The results are shown in Table 3.

Comparative Experiment C

Hydroformylation of styrene with $PPh_3$ and DIOP and Rh

Using either $PPh_3$ or DIOP (2,3-O-isopropylidine-2,3-dihydroxy-1,4-bis(diphenylphosphino)-butane) as ligands. The results are shown in Table 3.

TABLE 3

| Ligand | T(°C.) | pressure (MPa) | n/iso | % n-aldehyde | TOF (hr$^{-1}$)[b] |
|---|---|---|---|---|---|
| 2 | 60 | 1 | 0.77 | 44 | 128 |
| 2 | 80 | 1 | 0.88 | 47 | 724 |
| 2 | 120 | 1 | 2.35 | 70 | 4285 |
| $PPh_3$ | 70 | 6.2 | 0.08 | 7 | not determined |
| DIOP | 25 | 0.1 | 0.25–0.49[a] | 20–33[a] | not determined |

[a]Depending upon rhodium precursor used
[b]Turnover frequency in mol converted substrate per mol transition metal compound per hour.

EXAMPLE XI

Preparation of 4,6-bis(diphenylphosphino)-10,10dimethyphenoxasilin

At room temperature a solution of 8.00 g of diphenylether (47.0 mmol) in 35 ml of THF was added dropwise to a mixture of 41.4 ml of 2.5M n-butyllithium in hexane (103.4 mmol) and 16.7 ml of TMEDA (103.4 mmol). When all phenylether was added, the reaction mixture was stirred for 16 h. The ethereal solution of 2,2'-dilithiodiphenylether and a solution of 5.7 ml of dimethyldichlorosilane (47.0 mmol) in 75 ml of ether were added simultaneously to 40 ml of ether over 1 h. The reaction mixture was stirred for 16 hr. then hydrolyzed by addition of 30 ml of water. The hydrolyzed mixture was stirred for 2 hr. The organic layer was separated, and the aqueous layer was extracted with 30 ml of ether. The combined organic layers were treated with Norit, and dried with $MgSO_4$. The solvent was removed in vacuo. Small crystals formed during the concentration. The semisolid oil was crystallized form methanol, resulting in white crystals of 10,10-dimethylphenoxasilin with a grassy odour. Yield: 4.82 g (45%).

$^1$H NMR (CDCl$_3$) δ: 7.56 (dd, 2H, J=7.2, 1.7 Hz), 7.45 (dt,2H,J=7.7, 1.7 Hz), 7.22 (d, 2H, J=8.4 Hz), 7.17 (dt, 2H, J=7.2, 0.9 Hz), 0.51 (s,6H, (CH$_3$)$_2$Si); $^{13}$C($^1$H) NMR (CDCl$_3$) δ: 160.2, 134.5, 131.7, 123.1, 119.7 (C—Si), 118.5, 0.2 ((CH$_3$)$_2$Si); IR: CHCl$_3$ cm$^{-1}$): 3070, 3008 2957, 2901, 1604, 1593, 1574, 1426, 1370, 1301, 1270, 885, 845, 807; exact mass (MS): 226.0808 (calc. C$_{14}$H$_{14}$OSi: 226.0814).

At room temperature 12.6 ml of sec-butyllithium (1.3M in 98/2 cyclohexane/hexane, 13.3 mmol) was added dropwise to a stirred solution of 1.00 g of 10,10-dimethyphenoxasilin (4,42 mmol) and 2.1 ml of TMEDA (13.3 mmol) in 50 ml dry ether. When all sec-butyllithium was added the reaction mixture was stirred for 16 hours. Then solution of 2.6 ml of chlorodiphenylphosphine (13.3 mol) in 15 ml of hexanes was added dropwise, and the reaction mixture was stirred for 16 hours. The solvent was removed in vacuo, the resulting solid oil was dissolved in $CH_2Cl_2$, washed with water, dried with $MgSO_4$, solvent removed in vacuo. The resulting oil was washed with hexane, and crystallized from 1-propanol. The resulting white crystals are air stable. Yield: 1.78 g white crystals (68%).

$^1$H NMR ($CDCl_3$) δ: 7.50 (dd, 2H, J=7.2, 1.7 Hz, CHCHCSi), 7.16–7.31 (ar, 20H, $P(C_6H_5)_2$), 7.00 (t, 2H, J=7.3 Hz, PCCHCHCH), 6.79 (dq, 2H, J=7.5, 1.7 Hz, OCPCCH), 0.50 (s, 6H, $(CH_3)_2Si$); $^{31}P\{^1H\}$ NMR ($CDCl_3$) δ: −17.6; $^{13}C\{^1H\}$ NMR ($CDCl_3$) δ: 137.9 (t, J=6.8 Hz); through-space P—P coupling >60 Hz, 136.4, 134.5, 133.9 (t, J=10.6 Hz, P—C(Ph), 127.9, 127.3 (t, J=10.9 Hz, CO), 122.8, 118.5, −0.4 $((CH_3)_2Si)$; IR: ($CHCl_3$, $cm^{-1}$): 3059, 3007, 2960, 1580, 1572, 1434, 1399, 1370, 1120, 885, 857; exact mass (MS): 595.1741 (M+H) (calc. $C_{38}H_{32}OP_2Si$: 594.1698); mp:245°–245.5° C. Anal. Calcd. for $C_{38}H_{32}OP_2Si$: C, 76.75; H, 5.43. Found: C,76.04; H, 5.61.

EXAMPLE XII

Hydrocyanation of styrene with ligands 1, 2 and 4 and Ni 2.0 ml of a 73.3 mM solution of $Ni(COD)_2$ in toluene (0.147 mmol) was added to a Schlenk-vessel containing a stirring bar and 0.176 mmol of the ligand of Example I, II or XI. This reaction mixture was stirred for 2 hours, to ensure complete formation of the catalyst.

0.336 ml of styrene was added (433 mg, 4.15 mmol), and the reaction mixture was stirred for another 30 minutes. The reaction mixture was then cooled to ca. −40° C., 0.100 ml of liquid HCN (2.58 mmol) was added, and the Schlenk vessel was placed in a thermostated heating bath of the desired temperature.

After 19 hours, the stopper was removed to allow HCN (which was possibly still present) to evolve from the reaction mixture. After ca. 15 minutes the evolution of HCN was tested with a portable HCN-detector. When the concentration of HCN immediately above the Schlenk was below 5 ppm (MAC-value is 10 ppm), the crude reaction mixture was centrifuged, the supernatant weighed.

The reaction mixture was analysed with temperature controlled gas chromatography, using diphenylether and ethyl benzene as standards for the mass balance. The result with various ligands is depicted in the Table 4.

TABLE 4

| Ligand | Ligand/Ni | Temp °C. | time (hr) | Conversion % | Selectivity iso* % | Selectivity n* (%) | iso/n |
|---|---|---|---|---|---|---|---|
| 1 | 1.2 | 60 | 18 | 66 | 63 | 1.6 | 39.4 |
| 1 | 2.2 | 60 | 18 | 75 | 66 | 1.0 | 66.0 |
| 1 | 1.2 | 21 | 18 | 74 | 54 | 1.1 | 49.1 |
| 1 | 2.2 | 21 | 18 | 59 | 54 | 0.6 | 90.0 |
| 2 | 1.2 | 60 | 18 | 74 | 53 | 1.7 | 31.2 |
| 2 | 2.2 | 60 | 18 | 79 | 66 | 2.3 | 28.7 |
| 2 | 2.2 | 21 | 18 | 64 | 56 | 1.2 | 46.7 |
| 4 | 1.2 | 60 | 18 | 75 | 57 | 3.5 | 16.3 |
| 4 | 2.2 | 60 | 18 | 81 | 62 | 1.9 | 32.6 |
| 4 | 1.2 | 21 | 18 | 73 | 63 | 2.5 | 25.2 |
| 4 | 2.2 | 21 | 18 | 57 | 53 | 1.4 | 37.9 |

*n = 2-Phenyl-propionitrile;
iso = 1-Phenyl-propionitrile

Comparative experiment D
Hydrocyanation of styrene with Ni

Example XIII was repeated using DPPB, DPPE and DPPP as ligands. The results are shown in Table 5.

TABLE 5

| Ligand | L/Ni | T (°C.) | time (hr) | Conversion % | Selectivity iso* % | Selectivity n* % | iso/n % |
|---|---|---|---|---|---|---|---|
| DPPB[a] | 1.2 | 60 | 18 | 14 | 35 | 1.5 | 23.3 |
| DPPE[b] | 1.2 | 60 | 18 | 52 | 0.5 | 0.6 | 0.8 |
| DPPP[3] | 1.2 | 60 | 18 | 39 | 7 | 0.9 | 7.8 |

[a]1,4-Bis-diphenylphosphino-butane (DPPB)
[b]1,2-Bis-diphenylphosphino-ethane (DPPE)
[c]1,3-Bis-diphenylphosphino-propane (DPPP)
*see Table 4.

EXAMPLE XIV

Cross coupling between 2-BuMgCl and Bromobenzene with ligands 2 and 4 and Pd

To a suspension of 0.04 mmol (diphosphine) $PdCl_2$ in 10 ml of ether, 4 mmol of halide and 0.4 ml of decane (2.05 mmol, internal standard) were added, followed by 8 mmol of Grignard reagent in 10 ml of ether. The reaction vessel was kept at a constant temperature using a water bath.

At regular intervals ca. 1 ml of the reaction mixture was quenched in 1 ml of 10% aqueous HCl, and analysed by temperature controlled gas chromatography. The reported turn over frequencies were measured after 15 minutes.

The results with ligands from Experiment II and XI are given in Table 6.

TABLE 6

| Ligand | Temp (°C.) | Pd ($10^{-5}$ mol) | time (hr) | Conversion (%) | Sel. Cross Coupling[a] (%) | Sel. Homo Coupling[b] (%) |
|---|---|---|---|---|---|---|
| 2 | 0 | 4.0 | 0.25 | 3 | 56 | 44 |
| 2 | 0 | 4.0 | 23 | 100 | 79 | 21 |
| 2 | 20 | 3.3 | 0.25 | 5 | 60 | 40 |
| 2 | 20 | 3.3 | 4 | 9 | 60 | 40 |
| 4 | 20 | 4.1 | 0.25 | 9 | 86 | 14 |
| 4 | 20 | 4.0 | 0.25 | 13 | 83 | 17 |

[a]: i-Bu-benzene + n-Bu-benzene
[b]: Biaryl and octanes

EXAMPLE XIII

Carbonylation of butadiene with ligand 2 and Pd

A Parr autoclave, made of Hastelloy C, was filled successively with 0.18 mmol of palladium(II)acetate, 0.20 mmol of the ligand of Example II, 2.7 mmol of 2,4,6-trimethylbenzoic acid, and 19 g of diphenyl ether. The autoclave was closed and purged three times with 4.0 MPa carbon monoxide. Next, under a pressure of 1.0 MPa CO and with stirring at a speed of 1250 rpm, a mixture of 31 mmol methanol, 0.232 g nonane (internal standard for GC product analysis), 0.231 g of cyclohexane (internal standard for butadiene GC analysis), and 29 mmol of butadiene was injected under pressure from an injection vessel into the autoclave. The reaction mixture was brought to a temperature of 140° C. at a CO pressure of 6.5 MPa. After 1.5 hours the reaction mixture was analyzed for the butadiene and the reaction products by gas chromatographic methods. The conversion was: 59 %. The selectivity to methyl pentenoates was: 92 %.

What we claim is:

1. A bidentate phosphine ligand, the phosphorus atoms of the phosphine being connected via a bridge group, characterised in that the bridge group of the bidentate phosphine ligand consists of an ortho-anellated annular system, comprising two aryl groups, which aryl groups are connected by two bridges, a first bridge consisting of an —O— or an —S— atom and a second bridge being a group that contains an oxygen, sulphur, nitrogen, silicon or carbon atom or a combination of these atoms, the phosphorus atoms being connected to the two aryl groups of the bridge group at the ortho position relative to the —O— or —S— atom of the first bridge.

2. The bidentate phosphine ligand according to claim 1, characterised in that the second bridge in the bidentate phosphine ligand contains an —O—, —S—, —N($R^1$)—, —$N^+$($R^2$)($R^3$)—, —Si($R^4$)($R^5$)—, —P(O)($R^6$)—, or —C($R^7$)($R^8$)— group, or a combination of a —C($R^7$)($R^8$)— group with one of the groups mentioned, $R^1$ being a hydrogen atom, an organic group having between 1 and 20 carbon atoms or a polymer, $R^2$ and $R^3$ being organic groups, which may or may not be the same, having between 1 and 20 carbon atoms or a polymer, $R^4$ and $R^5$ being organic groups, which may or may not be the same, having between 1 and 10 carbon atoms, $R^6$ being a hydroxide group or an organic group having between 1 and 10 carbon atoms and $R^7$ and $R^8$ being organic groups, which may or may not be the same, having between 1 and 10 carbon atoms.

3. The bidentate phosphine ligand according to claim 1 or claim 2, characterised in that the bidentate phosphine ligand is represented by the following general formula (I):

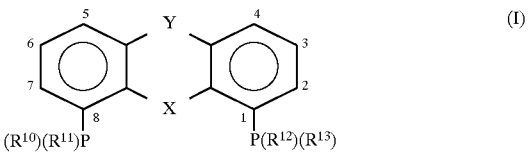
(I)

where X stands for the first bridge and Y for the second bridge and $R^{10}$, $R^{11}$, $R^{12}$ and $R^{13}$ stand for organic groups, which may or may not be the same, having between 1 and 14 carbon atoms.

4. The bidentate phosphine ligand according to claim 3, characterised in that X is an —O— atom.

5. The bidentate phosphine ligand according to claim 4, characterised in that Y does not represent an —O— atom.

6. The bidentate phosphine ligand according to claim 1 or 2, characterized in that the bidentate phosphine ligand is represented by the general formula (I)

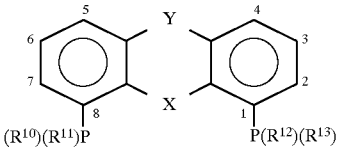

where X represents the first bridge, Y represents the second bridge and $R^{10}$, $R^{11}$, $R^{12}$ and $R^{13}$ represent aryl groups having between 6 and 14 carbon atoms, which may or may not be substituted.

7. The bidentate phosphine ligand according to claim 1 or 2, characterized in that the bidentate phosphine ligand is represented by the general formula (I)

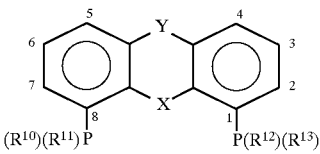

where X represents the first bridge and is an —O— group, Y represents the second bridge and $R^{10}$, $R^{11}$, $R^{12}$ and $R^{13}$ represent aryl groups having between 6 and 14 carbon atoms, which may or may not be substituted.

8. The bidentate phosphine ligand according to claim 1 or 2, characterized in that characterized in that the bidentate phosphine ligand is represented by the general formula (I)

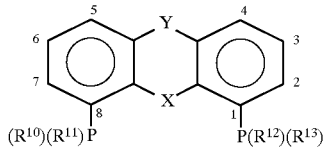

where X represents the first bridge and is an —O— group, Y represents the second bridge and does not represent —O—, and $R^{10}$, $R^{11}$, $R^{12}$ and $R^{13}$ represent aryl groups having between 6 and 14 carbon atoms, which may or may not be substituted.

9. The bidentate phosphine ligand according to claim 3, characterized in that $R^1$ represents an aralkyl group or an alkyl group.

10. The bidentate phosphine ligand according to claim 9, characterized in that $R^1$ is an alkyl group selected from the group consisting of methyl, ethyl, propyl, isopropyl, n-butyl and iso-butyl.

11. The bidentate phosphine ligand according to claim 9, characterized in that $R^1$ is a benzyl group.

12. The bidentate phosphine ligand according to claim 1, characterized in that the second bridge is represented by the formula —(N)($R^1$)— wherein $R^1$ represents an alkylidene group having between 2 and 20 carbon atoms.

13. The bidentate phosphine ligand according to claim 3, characterized in that $R^2$ and $R^3$ represent, independent of one another, an aralkyl or alkyl group.

14. The bidentate phosphine ligand according to claim 13, characterized in that $R^2$ and $R^3$ represent alkyl groups which are independently selected from the group consisting of methyl, ethyl, propyl, isopropyl, n-butyl, and iso-butyl.

15. The bidentate phosphine ligand according to claim 13, characterized in that one or both of $R^2$ and $R^3$ represent a benzyl group.

16. The bidentate phosphine ligand according to claim 1, characterized in that the second bridge is represented by the formula —N($R^2$)($R^3$)— wherein $R^2$ and $R^3$, independent of one another, represent an alkylidene group having between 2 and 20 carbon atoms.

17. The bidentate phosphine ligand according to claim 3, characterized in that $R^4$ and $R^5$, independent of one another, represent alkyl, aralkyl, alkaryl or an aryl group.

18. The bidentate phosphine ligand according to claim 17, characterized in that $R^4$ and $R^5$, independent of one another, represent an aryl or alkyl group.

19. The bidentate phosphine ligand according to claim 18, characterized in that $R^4$ and $R^5$, independent of one another, are selected from the group consisting of methyl, ethyl, propyl, isopropyl, n-butyl, iso-butyl, phenyl and benzyl.

20. The bidentate phosphine ligand according to claim 3, characterized in that $R^6$ represents an aryl, alkyl, aryloxy or alkoxy group.

21. The bidentate phosphine ligand according to claim 3, characterized in that $R^6$ is selected from the group consisting of phenyl, benzyl, methyl, ethyl, naphthyl, phenoxy, cyclohexyloxy and 2-tert-butylphenoxy.

22. The bidentate phosphine ligand according to claim 3, characterized in that $R^7$ and $R^8$, independent of one another, represent a group selected from the group consisting of methyl, ethyl, propyl, isopropyl, butyl, isobutyl, and phenyl.

23. The bidentate phosphine ligand according to claim 3, wherein $R^{10}$, $R^{11}$, $R^{12}$, and $R^{13}$ are independently selected from the group consisting of phenyl, naphthyl, diphenyl and cyclohexyl.

24. The bidentate phosphine ligand according to claim 3, characterized in that
R$^1$ is benzyl or an alkyl group selected from the group consisting of methyl, ethyl, propyl, isopropyl, n-butyl and iso-butyl;
R$^2$ and R$^3$, in independent of one another, are benzyl or an alkyl group selected from the group consisting of methyl, ethyl, propyl isopropyl, n-butyl and isobutyl;
R$^4$ and R$^5$, independent of one another, are selected from the group consisting of methyl, ethyl, propyl, isopropyl, n-butyl, iso-butyl, phenyl and benzyl;
R$^6$ is selected from the group consisting of phenyl, benzyl, methyl, ethyl, naphthyl, phenoxy, cyclohexyloxy, and 2-tertbutylphenoxy, and
R$^7$ and R$^8$, independent of one another, are selected from the group consisting of methyl, ethyl, propyl, isopropyl, butyl, isobutyl, and phenyl.

25. A method for the preparation of a bidentate phosphine ligand according to claim 1, said method comprising the combination of steps of:
dissolving an organic compound, which corresponds to the bridge group of the ligand, in a suitable solvent, together with a strong base and an additional complexing agent to obtain a mixture, and
adding two or more equivalents of an organic phosphorus compound to the mixture, said organic phosphorus compound optionally being dissolved in a solvent,
whereby said bidentate phosphine ligand is obtained.

26. The method according to claim 25, characterized in that said suitable solvent is at least one selected from the group consisting of diethyl ether, tetrahydrofuran, dioxane, hexane and cyclohexane.

27. The method according to claim 25, characterized in that said strong base contains a metal atom selected from the group consisting of lithium, potassium, sodium and magnesium.

28. The method according to claim 27, characterized in that said strong base is selected from the group consisting of n-butyl lithium, s-butyl lithium, and t-butyl lithium.

29. The method according to claim 25, characterized in that said dissolving step said strong base is added to said suitable solvent, said strong base addition being conducted at a temperature of −80° to 0° C.

30. The method according to claim 29, characterized in that said complexing agent for said strong base is added before or after adding said strong base to said suitable solvent.

31. A catalyst system containing a transition metal, and a bidentate phosphine ligand according to claim 1 or a bidentate phosphine ligand obtained according to claim 25.

32. A catalyst system according to claim 31, characterized in that said catalyst system is a complex of said transition metal and said bidentate phosphine ligand.

33. A catalyst system according to claim 32, characterized in that said transition metal is selected from the group consisting of Rh, Ru, Pd, Pt, Co, Ni, Fe, Mo and W.

34. A catalyst system according to claim 32, characterized in that said transition metal is selected from the group consisting of Co(I), Rh(I), Ru(II), and Ir(I).

35. The catalyst system according to claim 31, characterized in that the catalyst system contains said bidentate phosphine ligand and the transition metal compound in a molar ratio between 0.5 and 100.

36. The catalyst system according to claim 35, characterized in that the molar ratio is between 0.5 and 10.

37. The catalyst system according to claim 31, characterized in that said catalyst system contains a rhodium compound.

38. A method for preparing an aldehyde comprising hydroformylating an ethylenically unsaturated organic compound in the presence of carbon monoxide, hydrogen and a catalyst system containing a bidentate phosphine ligand and a transition metal compound according to claim 31.

39. The method for the preparation of an aldehyde according to claim 38, characterized in that the transition metal compound is a rhodium compound.

40. The method for the preparation of an aldehyde according to claim 31, characterized in that the ethylenically unsaturated organic compound has between 2 and 20 carbon atoms.

41. The method for the preparation of an aldehyde according to claim 38, characterized in that the ethylenically unsaturated compound is a terminally unsaturated organic compound.

42. A process for conducting a hydroformylation, hydrogenation, hydrocyanation, polymerization, isomerization, carbonylation, cross-coupling or metathesis reaction of at least one suitable organic compound, wherein said process is conducted in the presence of a catalyst system including a transition metal compound and a bidentate phosphine ligand, wherein said bidentate phosphine ligand is according to claim 1 or 2.

43. A process according to claim 42, characterized in that the bidentate phosphine ligand is represented by the general formula (I)

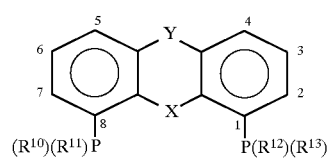

where X represents the first bridge, Y represents the second bridge and R$^{10}$, R$^{11}$, R$^{12}$ and R$^{13}$ represent organic groups, which may or may not be the same and which may or may not be substituted, having between 1 and 14 carbon atoms.

44. The process according to claim 43, characterized in that X is an —O— atom.

45. The process according to claim 44, characterized in that Y does not represent and —O— atom.

46. The process according to claim 43, characterized in that R$^{10}$, R$^{11}$, R$^{12}$ and R$^{13}$ are aryl groups having between 6 and 14 carbon atoms, which may or may not be substituted.

47. A process for the preparation of a pentenoic ester by carbonylation of butadiene in the presence of an alkanol and carbon monoxide and in the presence of a catalyst system containing a protonic acid with a pka>3, a palladium compound and a ligand according to claim 1 or 2.

48. A process according to claim 47, characterized in that the bidentate phosphine ligand is represented by the general formula (I)

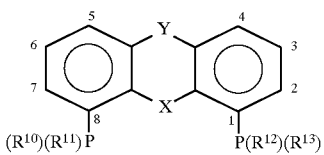

where X represents the first bridge, Y represents the second bridge and $R^{10}$, $R^{11}$, $R^{12}$ and $R^{13}$ represent organic groups, which may or may not be the same and which may or may not be substituted, having between 1 and 14 carbon atoms.

49. The process according to claim 48, characterized in that X is an —O— atom.

50. The process according to claim 49, characterized in that Y does not represent and —O— atom.

51. The process according to claim 48, 49 or 50, characterized in that $R^{10}$, $R^{11}$, $R^{12}$ and $R^{13}$ are aryl groups having between 6 and 14 carbon atoms, which may or may not be substituted.

* * * * *